United States Patent [19]

Cincotta et al.

[11] Patent Number: 5,679,685

[45] Date of Patent: Oct. 21, 1997

[54] ACCELERATED RELEASE COMPOSITION CONTAINING BROMOCRIPTINE

[75] Inventors: Anthony H. Cincotta, Andover, Mass.; Manuel Cincotta, Jr., Tiverton, R.I.; Christopher Louis Pelloni, Louisville, Colo.; Christopher Eric Runice, Denver, Colo.; Sandra Louise Tigner, Broomfield, Colo.

[73] Assignees: Ergo Science, Incorporated, Charlestown, Mass.; Geneva Pharmaceuticals, Inc., Broomfield, Colo.

[21] Appl. No.: 459,021

[22] Filed: Jun. 2, 1995

Related U.S. Application Data

[63] Continuation of Ser. No. 171,897, Dec. 22, 1993, abandoned.

[51] Int. Cl.[6] ............................ A61K 31/44; A61K 9/20
[52] U.S. Cl. ............................................. 514/288; 424/465
[58] Field of Search ............................. 514/288; 424/465

[56] References Cited

U.S. PATENT DOCUMENTS

| | | |
|---|---|---|
| 3,074,847 | 1/1963 | Bigsby . |
| 3,752,814 | 8/1973 | Fluckiger et al. . |
| 3,752,888 | 8/1973 | Fluckiger et al. . |
| 3,849,562 | 11/1974 | Richardson et al. . |
| 3,901,891 | 8/1975 | Fehr et al. . |
| 3,922,347 | 11/1975 | Bach et al. . |
| 4,054,660 | 10/1977 | Clemens et al. . |
| 4,151,283 | 4/1979 | di Salle et al. . |
| 4,219,555 | 8/1980 | Rucman et al. . |
| 4,239,763 | 12/1980 | Milavec et al. . |
| 4,659,715 | 4/1987 | Meier et al. . |
| 4,749,709 | 6/1988 | Meier et al. . |
| 4,783,469 | 11/1988 | Meier et al. . |
| 5,006,526 | 4/1991 | Meier et al. . |
| 5,128,145 | 7/1992 | Edgren et al. . |

FOREIGN PATENT DOCUMENTS

| | | |
|---|---|---|
| 890369 | 3/1982 | Belgium . |
| 32 16870 A1 | 11/1983 | Germany . |
| 57-82317 | 9/1990 | Japan . |
| 2192541 | 1/1988 | United Kingdom . |

OTHER PUBLICATIONS

Abu–Jayyab, *Med. Sci. Res.* 15:533–534, 1987.
Abu–Jayyab, *Chem. Abstracts* 107:173318r, 1987.
Babington et al., *Chem. Abstracts* 93(13):120448u, 1980.
Barnett et al., *Postgraduate Med. J.* 56:11–14, 1980.
Cincotta et al., *Life Sciences* 45:2247–2254, 1989.
De Mattia et al., *La Clin. Terap.* 164:21–26, 1983 (full document translation).
Gnudi et al., *Acta Diabetol. Latina* 14:119–128, 1977 (full document translation).
Larsen et al., *Chem. Abstracts* 109(9):6688w, 1988.
Mannelli et al., *Chem. Abstracts* 101(7):49205p, 1984.
Marken et al., *Clin. Pharm.* 11:851–856, 1992.
Meier et al., *Experientia* 48:248–253, 1992.
Thomas et al., *Sem. des Hosp. de Paris* 53(34–35):1857–1862, 1977 (abstract only translation).
International Search Report PCT US94/14994 Dated Apr. 10, 1995.

*Primary Examiner*—Shep K. Rose
*Attorney, Agent, or Firm*—Darby & Darby

[57] ABSTRACT

Disclosed herein is a solid oral dosage form comprising bromocriptine and one or more pharmaceutically acceptable excipients. The oral dosage form has a dissolution rate in excess of 90% in 5 minutes in 500 ml of 0.1N HCl aqueous medium at 37 C and is useful for adjusting the plasma prolactin profile of a patient.

7 Claims, 2 Drawing Sheets

1

ACCELERATED RELEASE COMPOSITION CONTAINING BROMOCRIPTINE

This is a continuation of application Ser. No. 08/171,897, filed Dec. 22, 1993, now abandoned.

FIELD OF THE INVENTION

This invention relates to compositions and solid oral dosage forms containing bromocriptine and providing a substantially faster dissolution profile than prior art bromocriptine dosage forms. In another aspect, the invention relates to methods for using these compositions in solid oral dosage forms.

BACKGROUND OF THE INVENTION

Solid oral bromocriptine preparations have long been commercially available as bromocriptine mesylate (PARLODEL®) in tablet and capsule form containing 2.5 and 5 mg of bromocriptine, respectively. These preparations are approved in the United States for use in the treatment of certain hyperprolactinemia-associated dysfunctions and acromegaly, in the prevention of physiological lactation, and in the treatment of Parkinson's disease and prevention of tolerance to Levodopa therapy for Parkinson's disease.

In these indications, the objective is to administer effective amounts of bromocriptine that will suppress prolactin throughout a 24-hour period. In fact, it has been reported that a 2.5 mg daily dose of bromocriptine is effective in suppressing prolactin to substantially uniform low levels throughout a 24-hour period.

Recently, in copending U.S. patent application Ser. No. 07/719,945 filed Jun. 24, 1991 (published as WO 93/00092 on Jan. 7, 1993) and in copending U.S. patent application Ser. No. 07/813,135 filed Dec. 23, 1991 (published as WO 93/12793 on Jul. 8, 1993), as well as in U.S. patent application Ser. No. 995,292 filed Dec. 22, 1992, administration of bromocriptine has been disclosed for an entirely different purpose, namely the modification of aberrant daily prolactin level rhythms so that they resemble, or more closely approximate in phase and amplitude, the normal daily plasma prolactin level rhythms of lean, young and healthy members of the same species and sex. (The disclosure of these applications is incorporated herein by reference.)

In humans, it has been determined that the normal healthy daily prolactin level profiles are highly regular and reproducible and are characterized by a low and relatively constant day level followed by a sharp night-time peak, returning to a low level by daytime. (See FIG. 1 which depicts the normal prolactin profiles for healthy young males and females on regular daily schedules.)

These prior applications disclose individualized therapeutic regimes for use in mammals by which a prolactin inhibitor (such as bromocriptine) is administered to a mammalian subject (particularly to a human) at a predetermined time during a 24-hour period if that subject has abnormally high daytime prolactin levels (at least 1 SEM higher than any of the normal daytime levels for the same sex). The administration and its timing are designed to decrease the subject's abnormally high daytime prolactin levels. (A prolactin stimulator may need to be administered at a different predetermined time during a 24-hour period, if the subject has abnormally low night-time prolactin levels, to increase these night-time prolactin levels to be preferably no lower than 1 SEM below the normal night-time prolactin levels for the same sex. It is also possible that both a prolactin inhibitor and a prolactin stimulator may need to be administered at different times to the same subject to bring about both a decrease in daytime prolactin levels and an increase in night-time prolactin levels.)

In the course of conducting human clinical trials, the inventors of these copending applications discovered that the commercially available solid oral bromocriptine preparations were not suitable for many human subjects because they depressed prolactin levels for prolonged periods of time which caused or worsened abnormally low prolactin levels at night-time. Because of its long lasting effect the commercially available bromocriptine dosage form did not permit a recovery in serum prolactin levels during night-time hours. As a result the prolactin profile of a subject that had ingested this dosage form remained somewhat abnormal.

Therefore, a need was identified for bromocriptine-containing compositions and solid oral dosage forms containing bromocriptine that would not suffer from this disadvantage, and would be effective in "sculpting" the patients plasma prolactin profiles to within low normal daytime levels without extending a substantial plasma prolactin-inhibitory effect into the night-time (or sleeptime hours). Furthermore, it was desired to develop solid oral dosage forms for such bromocriptine compositions because of the convenience of oral administration (as contrasted with use of e.g. the parenteral route of administration).

OBJECTS OF THE INVENTION

Accordingly, it is an object of the present invention to provide compositions and solid oral dosage forms containing bromocriptine that are effective in suppressing prolactin levels during a desired portion of a 24-hour period.

Another object of this invention is to provide a bromocriptine dosage form that acts faster than the commercially available bromocriptine dosage form in reducing serum prolactin levels in a mammal.

A further object of the present invention is a bromocriptine solid oral dosage form that has a faster dissolution rate than the commercially available bromocriptine solid oral dosage form.

It is a further object of the present invention to provide methods for more conveniently and accurately modulating aberrant prolactin level profiles that include too high prolactin levels during daytime.

These and other objects of the invention are accomplished in accord with the following disclosure.

SUMMARY OF THE INVENTION

The present invention comprises a solid oral dosage form containing bromocriptine, citric acid and one or more pharmaceutically acceptable excipients. The solid oral dosage forms of the invention are useful in the method of adjusting the prolactin profile of a patient having abnormally high levels of plasma prolactin in the daytime.

BRIEF DESCRIPTION OF THE DRAWING

FIG. 1 is not part of the present invention.

DETAILED DESCRIPTION OF THE INVENTION

Figure 1:
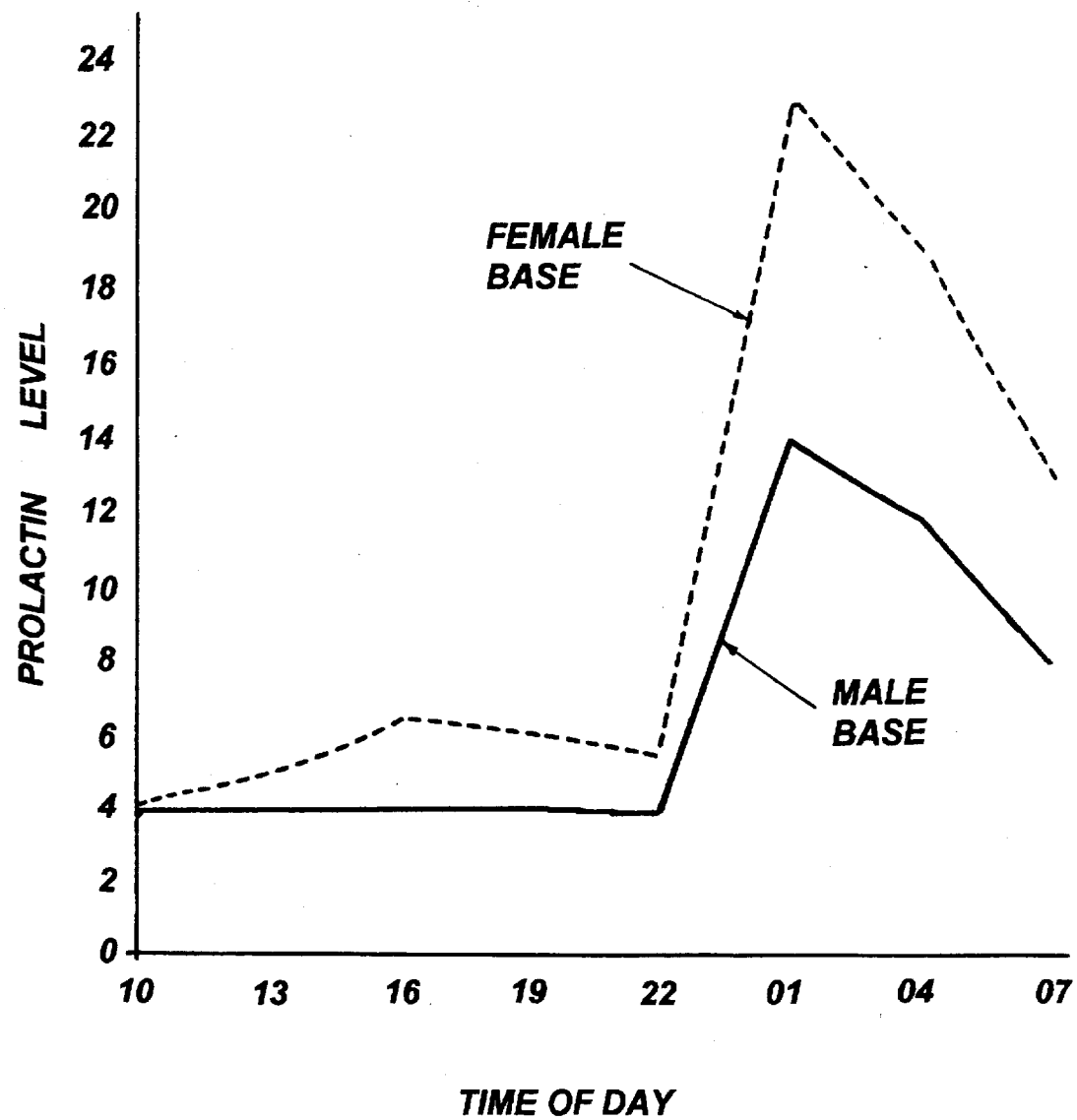
FIG. 1 is a graph in which the prolactin level is plotted versus time of day for healthy young males and healthy young females.

The present inventors determined that one of the problems with the commercially available bromocriptine preparation was that the amount of bromocriptine was too high and also that the long delay between oral administration of the drug and appearance of the principal biological effects of the drug (namely reduction in serum prolactin levels) made it difficult to employ the commercially available bromocriptine dosage form to modify a subjects aberrant prolactin level so that it resembles, or more closely approximates in phase and amplitude, the normal daily prolactin level rhythms of lean, young and healthy members of the same sex and species. This amount (2.5 mg) of PARLODEL suppressed many patients' prolactin levels to low levels from which they could not recover at night-time. The commercial preparations thus did not afford adequate control of the patients' prolactin profile. In addition, the amounts of bromocriptine contained in these preparations were poorly tolerated by a sizeable portion of the patient population over the course of therapy (which can last from several weeks to several months or even years).

Unexpectedly, the present inventors found that bromocriptine preparations that released bromocriptine at an accelerated rate (thereby resulting in reducing the time period between oral administration of the drug and appearance of its biological affects on serum prolactin titers) in the patient's bloodstream were more effective in modulating (or sculpting) prolactin profiles than preparations that released bromocriptine (even in substantially higher total amounts) more gradually.

By conducting experiments, the present inventors determined that by using a fast-release solid oral dosage form containing only 0.8 mg of bromocriptine, they could modulate aberrant daytime prolactin levels in a more controlled fashion in a substantially greater portion of the patient population. They found for example that fast release preparations containing only 0.8 mg of bromocriptine per dosage unit often were effective in bringing abnormally high daytime prolactin levels down to normal or near-normal levels for about at least a three-hour interval, and in some cases such small doses of bromocriptine were all that the patient required.

This was totally unexpected since a person of ordinary skill in the art would have surmised that the effectiveness of bromocriptine in reducing prolactin levels would be much more strongly dependent on the amount of bromocriptine administered. Instead, it was found that with a fast release preparation (i.e. one in which bromocriptine has a higher dissolution rate than for commercially available tablets), prolactin is reduced down to or closer to desired levels faster using a smaller amount of bromocriptine and that the duration of this reduction is a function of the amount of bromocriptine and the formulation in which it is administered. Use of these preparations was an improvement over use of higher amounts of slower-released bromocriptine in the commercial preparation.

Without wishing to be bound by any theory, it is believed that a rapid increase in the bloodstream concentration of bromocriptine appeared to be more important than the total amount of bromocriptine delivered to the blood stream. That is to say, it is believed to be most important to employ a dosage form in which bromocriptine is delivered into the bloodstream as rapidly as possible. This rapid bromocriptine release is believed to afford two benefits, namely (1) the ability to more precisely regulate the serum prolactin level of a subject and (2) enhanced ability to activate the nervous system in a time-dependent fashion (i.e. better resetting of neuroendocrine circadian rhythms).

The preparation of fast-release formulations containing bromocriptine presented problems because of the tendency of the active ingredient to isomerize and oxidize, especially in the presence of humidity.

After substantial experimentation with various known fast-release excipients, the present inventors achieved a stable fast-release formulation containing bromocriptine, an antioxidant, a filler, a disintegrating agent, a water scavenging agent and a lubricant.

A preferred formulation according to the invention has the following composition:

|  | Batch | (Dosage Form) |
| --- | --- | --- |
| bromocriptine mesylate USP | 149 g | (0.945 mg) |
| lactose NF | 11,867 g | (77.58 mg) |
| citric acid USP | 212 g | (1.35 mg) |
| corn starch NF | 1,413 g | (9.0 mg) |
| colloidal silicon dioxide NF | 71 g | (0.45 mg) |
| magnesium stearate NF | 106 g | (0.675 mg) |
|  | 13,818 g | 90.0 mg |

The foregoing composition can be used to make tablets containing 0.945 g of bromocriptine mesylate (equivalent 0.8 mg of anhydrous bromocriptine) providing a desirably fast rate of release combined with a desirably small amount of active ingredient. The small amount of active ingredient enables fine-tuning of the appropriate dosage for each patient. Use of anhydrous lactose filler is preferred to minimize moisture content. Citric acid is an antioxidant. Corn starch is a disintegrating agent. Colloidal silicone dioxide does not act as a flowing agent in this amount but as a water-scavenger. Magnesium stearate acts as a lubricant. These are non-limiting examples of the foregoing compounds.

The composition and dosage form of the present invention can be prepared according to various methods known in the art. One such preferred method is the following:

Bromocriptine mesylate and part of the lactose (the quantity of lactose is approximately three times the amount of bromocriptine mesylate) are mixed together and screened through a 20 mesh screen to help disperse the active ingredient. Then this mixture, along with the remaining lactose, citric acid, and corn starch are mixed for one minute in a Fielder high shear mixer. Magnesium stearate and colloidal silicon dioxide are then each mixed with an approximately equal amount of the previous mixture and screened through a 20 mesh screen. This mixture is then layered into a V-blender with the remaining mixture from the Fielder mixer, and blended for two minutes. The final blend is compressed into 5/16" diameter tablets.

The dissolution profile of a tablet according to the invention containing 0.8 mg bromocriptine (0.945 mg of the mesylate derivative) has been compared below to that of PARLODEL (2.5 mg) in 500 ml 0.1N HCl at 37±0.5 C using USP Apparatus 1 (Baskets) at 120 rpm. The results were as follows:

| TIME |  | 5 | 15 | 30 | 45 | minutes |
| --- | --- | --- | --- | --- | --- | --- |
| Pres. Inv. 0.8 mg | Avg of 12 Units | 95 | 100 | 101 | 100 | % |
| Parlodel 2.5 mg | Avg of 12 Units | 20 | 54 | 90 | 97 | % |

From the above table, it can be readily appreciated that the dissolution rate of the present dosage form is much faster than the release rate of the commercial PARLODEL tablet (the two types of tablets are of essentially the same size).

Experiments were conducted on patients having abnormally high daytime prolactin levels as follows:

One group of three patients were administered PARLODEL (2.5 mg) at 8:30 am; another group of three patients were administered one 0.8 mg fast release bromocriptine tablet according to the present invention (total dose 0.8 mg bromocriptine) at 8:30 am; a third group of three patients were administered two 0.8 mg fast release bromocriptine tablets according to the present invention (total dose 1.6 mgs bromocriptine) at 8:30 am; a fourth group of three patients were administered three 0.8 mg fast release bromocriptine tablets according to the present invention (total dose 2.4 mgs bromocriptine) also at 8:30 am. Finally, a fifth group were administered four 0.8 mg fast release bromocriptine tablets (total dose 3.2 mgs bromocriptine) of the present invention at 8:30 am. The patients all had abnormally high daytime prolactin levels but both the extent of the daytime abnormality (how much it was over the normal, whether there were one or several daytime "peaks") and the co-presence of a night-time abnormality varied. Also, the responsiveness of each patient to bromocriptine was not taken into account. In other words, the patients were selected randomly.

From these experiments, the following qualitative conclusions were drawn:

(1) The rate at which prolactin was suppressed was better for patients treated with only 1.6 mg of the quick release bromocriptine composition than for patients treated with 2.5 mg of PARLODEL with only 1.6 mg of the present quick release bromocriptine composition despite the substantial difference in the amount of active ingredient. This shows that the fast-release bromocriptine composition of the invention achieves a better rate of prolactin suppression with a substantially smaller amount of active ingredient and that the release rate of active ingredient is important in determining the rate of prolactin suppression.

(2) The duration of maximum suppression appeared to vary proportionately with the amount of bromocriptine administered (for the four doses of the present invention described above).

(3) The duration of maximum suppression for the patients receiving 2.4 mg of the present composition was longer than that for the patients receiving 2.5 mg of PARLODEL yet the amounts administered in each case were about the same and would have been expected to be physiologically indistinguishable. As such, 1.6 mgs of bromocriptine delivered according to the present invention will produce the desired effect on inhibition of the diurnal plasma prolactin level without inhibiting the nocturnal prolactin level (as would occur with the 2.5 mg PARLODEL tablet).

The fast release bromocriptine tablets of the present invention can be administered as appropriate depending on the desired changes that need to be effected to the patient's prolactin profile. The total number of tablets (of 0.8 mg) administered to a particular patient and the time of administration will vary depending on the individual patients' plasma prolactin profile.

With the present formulation, it is thus possible to administer to a patient two 0.8 mg tablets together early in the morning, or one 0.8 mg tablet early in the morning and one later in the morning (e.g. about noon) or two tablets early in the morning and one later in the morning, depending on the effect desired on the prolactin profile. In a preferred embodiment of the invention two 0.8 mg fast release bromocriptine tablets according to the present invention are ingested orally during the early morning (day) hours.

The method of administering the fast release bromocriptine oral dosage forms of the present invention to modify an aberrant daily prolactin level rhythm in a human is illustrated by the following example.

Figure 2:
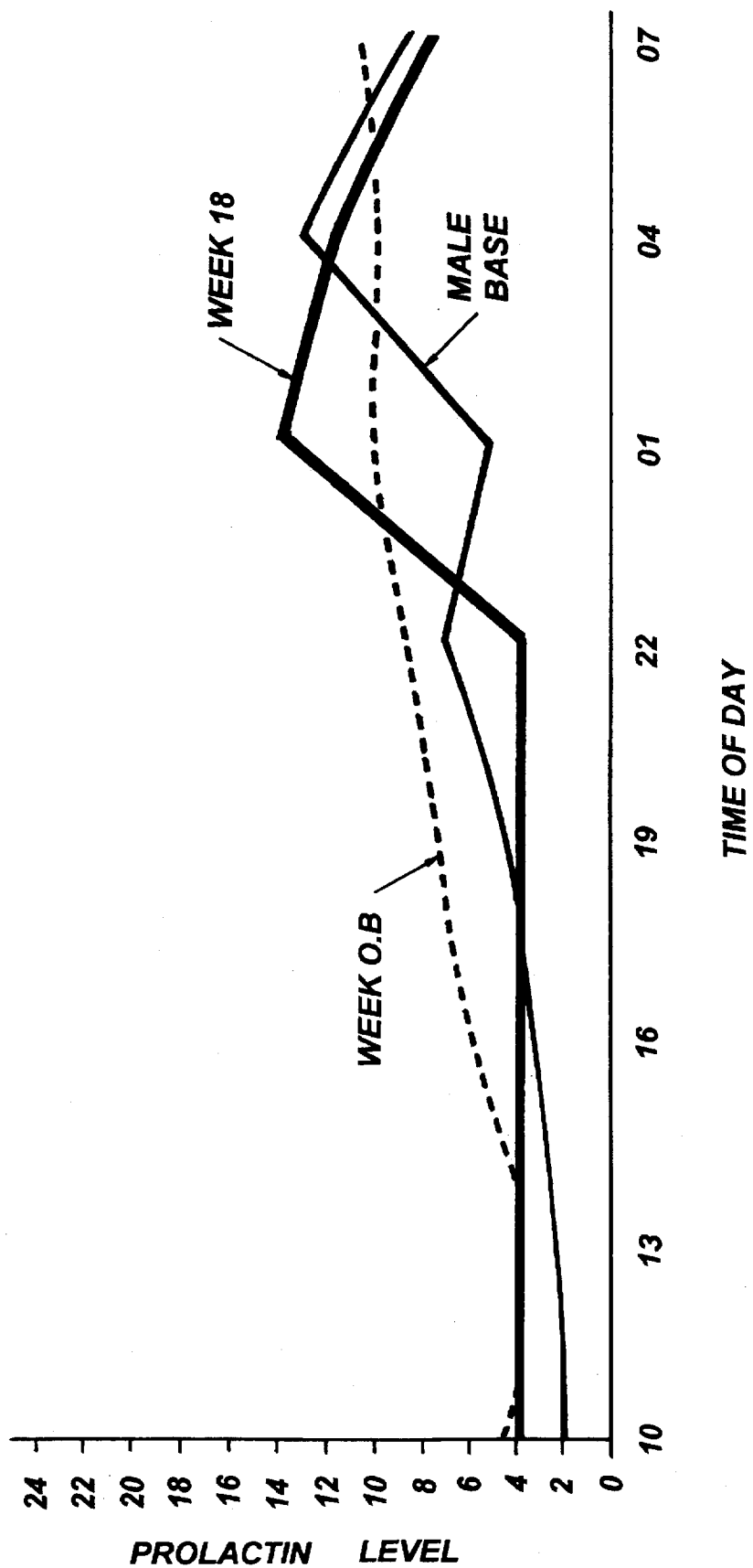
FIG. 2 is a graph illustrating the prolactin profile of a patient at various dates. For each date the prolactin level is plotted versus time of day. The normal prolactin profile for a healthy subject of the same sex is also plotted.

A human patient diagnosed as having an aberrant plasma prolactin daily level received bromocriptine via the oral route for a period of 18 weeks. For the first two weeks of treatment the patient orally ingested one 0.8 mg fast release bromocriptine tablet having the preferred bromocriptine formulation disclosed above at 5 AM (0500 hours) daily and two more of such tablets at 9:30 AM (0930 hours) daily. Starting in the third week and continuing daily through the end of week 18 the patient ingested one 0.8 mg fast release bromocriptine tablet prepared according to the preferred embodiment disclosed above, at 5 AM (0500 hours) and a second such tablet at 9:30 AM (0930 hours). The patients baseline prolactin level (at week 0 "week 0.B" on FIG. 2), the normal prolactin level ("male base") and the patients prolactin level at the end of week 18 after the start of treatment ("week 18" on FIG. 2) are shown in the graph in FIG. 2. Referring to FIG. 2 it can be seen that the patient initially had a daytime prolactin level that was more than 1 SEM above normal and a depressed night-time prolactin level. After 18 weeks of treatment according to the present invention, the patients aberrant prolactin rhythm had been modified to more closely approximate in phase and amplitude the normal daily prolactin level rhythm (as illustrated on the graph of FIG. 2).

Referring to the plot on FIG. 2 (illustrating the patients' prolactin profile at the end of week 18) it can be seen that the daytime prolactin level has been lowered but that the night-time prolactin level had been increased and more closely resembles the normal night-time prolactin profile as illustrated by the normal plot on FIG. 2.

What is claimed is:

1. A solid oral dosage form comprising bromocriptine (B) as the sole pharmaceutically active ingredient and physiologically acceptable inert excipients including a group of excipients that affect the rate of bromocriptine release from said dosage form wherein said release affecting excipients consist of citric acid (C) and a disintegrating agent (D).

2. The dosage form of claim 1 wherein the disintegrating agent (D) comprises cornstarch, and the dosage form further comprises the inert excipients lactose, colloidal silicon dioxide and magnesium stearate.

3. The dosage form of claim 2 wherein the relative amounts of said bromocriptine and said release affecting excipients are 0.8 mg bromocriptine; 1.35 mg of citric acid; and 9 mg corn starch, and the relative amounts of the inert excipients are 77 mg anhydrous lactose; 0.45 mg colloidal silicon dioxide; and 0.675 mg magnesium stearate.

4. The solid oral dosage form of claim 1 further comprising a low moisture content filler, a water-scavenging agent and a lubricant.

5. The oral dosage form of claim 4 wherein said dosage form has a total weight of about 90 mgs.

6. A solid oral dosage form consisting of bromocriptine (B); as an antioxidant, citric acid (C); a low moisture content filler, a disintegrating agent (D), a water-scavenging agent and a lubricant, wherein said B, C, and D are at a weight ratio B:C:D of 0.8:1.35:9.

7. The solid oral dosage form of claim 6 wherein (D) is cornstarch.

* * * * *